United States Patent [19]
Ala-Kleme et al.

[11] Patent Number: 6,136,268
[45] Date of Patent: Oct. 24, 2000

[54] METHOD FOR LUMINESCENCE MEASUREMENTS

[75] Inventors: Timo Ala-Kleme, Mellilä ; Keijo Haapakka, Rusko; Pentti Juhala, Kuusisto; Jouko Kankare, Turku; Sakari Kulmala, Littoinen; Rainer Käppi, Turku; Kari Loikas; Mauri Nauma, both of Raisio; Jyrki Pihlaja, Paimio; Timo Sutela; Raili Valli, both of Turku, all of Finland

[73] Assignee: Orion Diagnostica, Espoo, Finland

[21] Appl. No.: 09/376,139

[22] Filed: Aug. 17, 1999

[51] Int. Cl.$^7$ ............... G01N 21/76; G01N 21/29; G01N 24/00; G01N 21/00; G12Q 1/68

[52] U.S. Cl. ............... 422/52; 422/82.05; 436/172; 436/164; 435/6

[58] Field of Search ............... 422/52, 82.05; 436/172, 164; 435/6

[56] References Cited

U.S. PATENT DOCUMENTS

| | | | |
|---|---|---|---|
| 5,147,806 | 9/1992 | Kamin et al. | 436/149 |
| 5,308,754 | 5/1994 | Kankare et al. | 435/7.4 |
| 5,384,265 | 1/1995 | Kidwell et al. | 436/525 |
| 5,434,088 | 7/1995 | Ikeda et al. | 436/525 |
| 5,527,710 | 6/1996 | Nacamulli et al. | 436/517 |
| 5,637,508 | 6/1997 | Kidwell et al. | 436/525 |
| 5,705,402 | 1/1998 | Leland et al. | 436/526 |
| 5,744,376 | 4/1998 | Talley et al. | 436/172 |
| 5,746,974 | 5/1998 | Massey et al. | 422/52 |
| 5,779,976 | 7/1998 | Leland et al. | 422/52 |

FOREIGN PATENT DOCUMENTS

| | | |
|---|---|---|
| 0658760 | 6/1995 | European Pat. Off. . |
| 0962773 | 8/1999 | European Pat. Off. . |
| 8190801 | 7/1996 | Japan . |
| 2217007 | 10/1989 | United Kingdom . |
| 8602734 | 5/1986 | WIPO . |
| 9005301 | 5/1990 | WIPO . |
| 9214138 | 8/1992 | WIPO . |
| 9214139 | 8/1992 | WIPO . |
| 9615440 | 5/1996 | WIPO . |
| 9628538 | 9/1996 | WIPO . |
| 9641177 | 12/1996 | WIPO . |

OTHER PUBLICATIONS

Olsvik O et al, "Magnetic separation techniques in diagnostic microbiology", Clinical Microbiology Reviews, Jan. 1994, vol.7, No. 1, pp. 43–54.

Forbes, G.A. et al., "On–line electrogenated Ru(bpy)$_3^{3+}$ chemiluminescent detection of β–blockers separated with capillary electrophoresis", Anal. Chim. Acta, 347, 289–93 (2997).

Skotty, D.R. et al., "Determination of Dansyl Amino Acids and Oxalate by HPLC and Electrogenated Chemiluminescence Detection Using Tris(2,2'–bipyridyl) ruthenium (III) in the Mobile Phase", Anal. Chem., 68, 1530–35 (1996).

Kankare, J. et al., "Novel labeling agents for immunoassay by time–resolved electrogenerated chemiluminescence", Anal. Chim. Acta, 295, 27–35 (1994).

Kankare J., et al., "Immunoassay by time–resolved electrogenerated luminescence", Anal. Chim. Acta, 266, 205–12 (1992).

Kankare, J., "Cathodically induced time–resolved lanthanide(III) electroluminescence at stationary aluminum disc electrodes", Anal. Chim. Acts, 256, 17–28 (1992).

Haapakka, K., et al., "Fluorophor–enhanced Cathodic Electroluminescence at an Oxide–covered Aluminum Electrode", Anal. Chim. Acta, 207, 195–210 (1988).

Fleischmann, M., et al., "Electrochemical Behavior of Dispersion of Spherical Ultramicroelectrodes. 1. Theoretical Considerations", J. Phys. Chem., 89, 5530–36 (1985).

Haapakka, K., et al., "Feasibility of Low–voltage Cathodic Electroluminescence at Oxide–covered Aluminum Electrodes for Trace Metal Determinations in Aqueous Solutions", Anal. Chim. Acta, 171, 259–67 (1985).

Ege, D., et al., "Electrogenerated Chemiluminescent Determination of Ru(bpy)$_3^{2+}$ at Low Levels", Anal. Chem., 56, 2413–17 (1984).

Haapaka, K. E. and Kankare J. J., "The Mechanism of the Electrogenerated Chemiluminescence of Luminol in Aqueous Alkaline Solution", Anal. Chim. Acta, 138, 263–75 (1982).

Goodridge, F. et al., "The Behavior of Bipolar Packed–Bed Electrodes", Electrochim. Acta, 22, 347–51 (1977).

Eardley, D.C., et al., "Bipolar Electrolysis with Intra Phase Conduction in Two Phase Media", Electrochim. Acta, 18, 839–48 (1973).

Harvey, N., "Luminescence During Electrolysis", J. Phys. Chem., 33, 1456–59 (1929).

Primary Examiner—John S. Brusca
Assistant Examiner—Stephen Siu
Attorney, Agent, or Firm—Baker Botts L.L.P.

[57] ABSTRACT

A method for determining the concentration of a light-emitting compound. An electric pulse is applied to a pair of current-delivering electrodes immersed in an electrolyte having positioned between the electrodes a conductor not in electronic contact with electrodes. As a result of the applied electric pulse, the light-emitting compound in electronic contact with the conductor luminesces in which the emitted light is measured and used to quantify the light-emitting compound.

23 Claims, 4 Drawing Sheets

METHOD FOR LUMINESCENCE MEASUREMENTS

FIELD OF INVENTION

The present invention pertains to a method of assaying the concentration of a light-emitting compound through luminescence and, more particularly, to a method of assaying the concentration of a light-emitting compound through electrogenerated chemiluminescence.

BACKGROUND OF THE INVENTION

There is an expanding need for specific, sensitive, rapid and cost effective methods of detecting and quantifying chemical, biological and biochemical substances such as antibodies, hormones, viruses, enzymes, metabolites, narcotics, poisons, drugs, microorganisms and nucleic acids. The required sensitivity and specificity are obtained by using binding reactions, e.g., antigen-antibody reactions where the presence of the complex of diagnostic value i.e., analyte, is indicated by means of a detectable label attached to one or more of the complexing materials. An example of commercially useful labeling compounds are those capable of generating a luminescence based on the photochemical, chemical or electrochemical excitation methods.

The analytical methods based on luminescence in its various modifications are generally known for their sensitivity, but each have their own shortcomings at very low concentrations of the emitting species. The sensitivity of fluorescence is limited by Raleigh and Raman scattering phenomena and as well as fluorescent impurities which increase the non-specific background emission. Phosphorescence is mainly restricted to solid state and the emission from those very few compounds which have room temperature phosphorescence in solution is generally extremely sensitive to oxygen, which hampers their practical applications. The method based on conventional fluorescence and phosphorescence use an excitation by light and need an appropriate light source and optics. The methods based on chemiluminescence do not need excitation optics and the instrumentation is generally very simple. However, chemiluminescence methods are often subjects to serious chemical interference. The method based on an instrumentally simple electrochemical excitation (i.e., electrogenerated chemiluminescence or ECL) utilizes an excitation by an electrical pulse applied to an electrode which provides a low detection limit.

ECL of inorganic and organic compounds in electrolyte solutions is well known in the art. For instance, the anodic ECL of luminol at the platinum electrode in an aqueous electrolyte has been studied since 1929 (for instance, N, Harvey, J. Phys. Chem. 33 (1929) 1456; K. Haapakka and J. Kankare, Anal. Chim. Acta 138 (1982) 263), an anodic ECL of $Ru(bpy)_3^{2+}$ in the presence of oxalate in an aqueous electrolyte and a cathodic ECL of $Ru(bpy)_3^{2+}$ in the presence of peroxydisulfate in an acetonitrile/water mixture have been reported by Bard et al. (D. Ege, W. Becker and A. Bard, Anal. Chem. 56 (1984) 2413), a cathodic ECL of numerous inorganic ions (K. Haapakka, J. Kankare and S. Kulmala, Anal. Chim. Acta 171 (1985) 259) and numerous organic compounds (K. Haapakka, J. Kankare and O. Puhakka, Anal. Chim. Acta 207 (1988) 195) at an oxide-covered aluminium electrode in aqueous electrolytes containing an appropriate oxidizing agent have been reported, where the short-lived ECL is measured during the electric pulse applied to the electrodes. A variety of terbium(III) complexes are capable of initiating a long-lived terbium(III)-specific cathodic ECL at an oxide-covered aluminium electrode in an aqueous electrolyte containing peroxydisulfate, which makes possible to eliminate the short-lived background ECL by using a time-resolved ECL detection thus creating the basis for extreme trace analysis (J. Kankare, K, Faldén, S. Kulmala and K. Haapakka, Anal. Chim. Acta 256 (1992) 17; J. Kankare, A. Karppi and H. Takalo, Anal. Chim. Acta 295 (1994) 27). Binding assays of the analytes of interest based on the measurement of ECL at the electrode surface have been proposed: for instance, A. Bard et al. (D. Ege, W. Becker and A. Bard, Anal. Chem. 56 (1984) 2413 and WO 86/02734) have suggested ruthenium(III)- and osmium(III)-containing ECL labels; J. Kankare and K. Haapakka (GB 2217007 B, U.S. Pat. No. 5,308,754), J. Kankare, K. Haapakka, S. Kulmala, V. Nänto, J. Eskola and H. Takalo, Anal. Chim. Acta 266 (1992) 205 and M. Billadeau et al. (WO 96/41177) have suggested the use of Ln(III)-containing ECL labels (Ln(III)=Dy(III), Eu(III), Sm(III), Tb(III)) in the binding assays based on the time-resolved ECL. Numerous sample cell configurations and methods of measurement for the ECL detection have been proposed where the ECL is generated either at the surface of the electrode (for instance in EP 65 8760 A1 and WO 96/28538) or at the surface of magnetic beads collected onto the surface of the electrode (for instance in NVO 92/14139; WO 92/14138, JP 08190801 A2 and WO 96/15440). The ECL detectors have been applied in High Pressure Liquid Chromatography (for instance, D. Skotty, W. Lee and T. Nieman, Anal. Chem. 68 (1996 1530) and in Capillary Electrophoresis (for instance, G. Forbes, T. Nieman and J Sweedler, Anal. Chim. Acta 347 (1997) 289).

Typically for ECL, the luminescent compound must be in the close proximity of the electrode surface. Especially as to the ECL immunoassays, the ECL label, which contains luminescent compound attached to antibody or antigen, is bound to the electrode surface, e.g., by the direct immunoreaction where one of the immunoreagents is immobilized on the electrode surface (J. Kankare and K. Haapakka, GB 2217007 B, U.S. Pat. No. 5,308,754), or indirectly by utilizing non-conducting magnetic beads coated with immunoreagents, which after the immunoreaction has occurred, are collected at the electrode surface by a magnetic field. The advantage of using these magnetic beads is a considerably more efficient binding reaction as compared to that, e.g., in the antibody-coated planar electrode surface. However, use of magnetic beads in ECL assays are not without disadvantages: (i) the excitation efficiency is often low because of the an excitation distance of around 25 Å or less from the electrode surface is required (see, e.g., WO 92/14139): (ii) the efficiency of detecting the emitted light from the proximity of the electrode surface is hindered by the light-shielding bead layer and (iii) the magnetic beads detach from the electrode surface during the short excitation pulse thereby inhibiting excitation efficiency.

While magnetic beads do provide an improvement over conventional ECL methods, there is still a need in the art for ECL assays that exhibit further increased sensitivity. Accordingly, it is an object of the present invention to provide an ECL method having increased sensitivity.

SUMMARY OF THE INVENTION

The present invention provides a method for measuring the concentration of a luminescent compound with improved sensitivity. The method includes providing an electrolyte having immersed therein a pair of current-delivering electrodes with an electrically conductive material positioned between the electrodes, but not in electronic contact with the electrodes, and a luminescent compound. An electric current is then applied to the electrodes to induce the luminescent compound in electronic contact with the electrically conductive material to luminesce. The luminescence (i.e., emitted-light) is measured to ascertain the concentration of the luminescent compound.

Examples of the electrically conductive material include, but are not limited to, electrochemically inert materials and insulated metals, alloys or semi-metals or combinations thereof. Representative electrochemically inert materials are glassy carbon, gold, platinum, or mixtures thereof. Representative insulated metals or semi-metals are aluminum, hafnium, magnesium, silicon, tantalum, titanium, zirconium, or mixtures thereof. Preferably the insulating material is an oxide-coating. In one embodiment the electrically conductive material is a porous membrane covered with a thin layer of the electrochemically inert material or the insulated metal or semi-metal.

The electrolyte is a non-aqueous or aqueous electrolyte. The luminescent compound is attached to the surface of the electrically conductive material or alternatively is bound to an analyte of interest (e.g., a nucleic acid or amino acid sequence). In one embodiment, luminescence is measured after a delay from the end of a electrical pulse being applied to the current-delivering electrodes. In other embodiments, luminescence is induced using at least two different electrochemiluminescent compounds, at least two different types of electrically conductive materials or at least two different analytes of interest.

Advantageously, the method of the present invention provides an ECL assay with increased sensitivity. Other advantages includes the ability to assay the concentration of multiple analytes of interest and to provide internal standardization. These and other advantages will become apparent from the description set forth below.

DETAILED DESCRIPTION OF THE INVENTION

The present invention provides an unique method for measuring the concentration of a luminescent compound with increased sensitivity. This method as further described below is hereinafter referred to as Contactless Electrogenerated Luminescence or COEL.

In accordance with the present invention, an electrolyte containing a luminescent compound is provided having immersed therein a pair of current-delivering electrodes. An electrically conductive material is positioned between the current-delivering electrodes, but not in electronic contact with the electrodes. Electronic contact in this context means both physical contact and being within the requisite excitation distance to induce luminescence of a luminescent compound, which is preferably 25 Å or less. An electric current is generated between the electrodes inducing the luminescent compound within electronic contact of the electrically conductive material to luminesce. Thus, contrary to previous ECL methods, light emission can generated without the luminescent compound being in electronic contact with the current delivering electrodes. The luminescence (i.e., light-emission) is measured following conventional techniques to ascertain the concentration of luminescent compound.

The electrically conductive material (hereinafter the "conductor") is any electrically conductive material that does not detrimentally react with the electrolyte. The conductor should have a conductivity equal to, preferably greater than, the conductivity of the electrolyte. While wishing not to be bound by theory, it is believed that a faradaic current is generated through the conductor by causing a voltage drop in the electrolyte when a current is generated between the current-delivering electrodes. This method of generating a faradaic current is also known as bipolar electrolysis as set forth in Eardley, D. Handley and S. Andrew, Electrochim. Acta 18 (1973) 839; F. Goodridge, C. King and A. Wright, Electrochim. Acta 22 (1977) 347; M. Fleischmann, J. Ghoroghchian and S. Pons, J. Phys. Chem. 89 (1985) 5530).

Preferably, the conductor is made from an electrically conductive material used for electrodes in ECL assays. For example, the conductor can be an electrochemically inert material such as glassy carbon, gold, platinum, stainless steel or a combination thereof. The conductor can also be an insulated metal, alloy, semi-metal or any combination thereof. Specific examples of metals or semi-metals include, but are not limited to, aluminum, hafnium, magnesium, silicon, tantalum, titanium, zirconium, or any combination thereof. In this context, insulated means that the metal, alloy or semi-metal is insulated (i.e., covered) with an protective coating such as an oxide or polymer coating. The coating can range from 1 to 100 nanometers, as with oxide-covered electrodes used in known ECL assays.

As will be apparent to those skilled in the art, the choice of material for the conductor is dependent on the type of ECL reaction used to generate luminescence. For example, if an anodic ECL reaction will be used to initiate luminescence an electrochemically inert material is selected. On the other hand, if a cathodic ECL reaction will be used to initiate luminescence an insulated metal, alloy or semi-metal is selected.

The conductors of the present invention can also contain additional non-conductive components to alter the physical properties of the conductor. For example, the conductor can have a polymeric core to decrease the density of the conductor to allow it to be suspended in the electrolyte. Likewise, the conductor can have a core formed from a magnetic metal or alloy to aid in collection of the conductor. Known magnetic metals and alloys can be used, such as those listed in the Handbook of Chemistry and Physics, 70th ed., CRC press, which is incorporated herein by reference.

In accordance with the present invention, the conductor can have any shape or size. For example, the conductor can have a spherical or elliptical shape. Electrically conductive materials shaped as spheres are readily available from commercial sources such as AbbotBall Company, located in Connecticut, USA. The spherical conductors can range in size from 10 $\mu$m to 10 mm. Likewise, the conductor can be a porous matrix having thereon the electrochemically inert material, or the insulated metal or semi-metal.

Optionally, the electrolyte can contain conductors of differing shapes, sizes and electrically conductive materials to provide alternating threshold potentials for inducing luminescence. For example, as will be apparent to those skilled in the art following the teachings of the invention, conductors formed from differing materials, such as gold and aluminum, will have different threshold potentials for initiating luminenscence of a luminescent compound (i.e., an ECL moiety) in electronic contact with the conductor. Likewise, conductors having differing sizes will also exhibit different threshold potentials for initiating luminenscence of ECL moiety. This unique aspect of the inventions allows for multiple ECL reactions to conducted in the same electrolyte, which in turn facilitates internal standardization and the assay of multiple analytes of interest.

The electrolyte is any electrolyte used for ECL reactions. In accordance with the present invention the electrolyte can be an aqueous or non-aqueous electrolyte. The choice of the electrolyte is partially determined by factors such as the analyte to be detected and the ECL moiety to be used. For example, if the concentration of a biomolecules (e.g., nucleic acid or protein) is to be ascertained, a buffered aqueous electrolyte is selected. Such parameters can easily be determined by one skilled in the art.

In accordance with invention, the ECL moiety is any luminescent moiety used for ECL assays. Accordingly, the ECL moieties are preferably metal chelates. Examples of metal chelates to be used include, but are not limited to, chelates of transition or rare earth metals such as ruthenium, terbium, osmium, rhenium, iridium, rhodium, platinum, indium, palladium, molybdenum, technetium, copper, chromium, tungsten, or combinations thereof. Two especially preferred chelates are ruthenium and terbium chelates.

The current delivering electrodes are made from any electrically conductive materials used for electrodes in ECL reactions. Accordingly, the electrodes can be formed from the same electrically conductive materials used to form the conductors as described above. In one embodiment of the invention, the electrodes and the conductor are of the same material. In another embodiment, the current delivering electrodes are made from electrically conductive materials on which no ECL emission is possible to minimize background emission. Preferably, the electrodes are spaced distally from each other.

An electric current is generated by applying an appropriate voltage to the current-delivering electrodes for a predefined time frame, which results in a partial current flow through the conductor causing the ECL moiety in electronic contact with the conductor to luminesce. The requisite voltage (i.e., threshold potential) to induce luminescence is dependent on the interfacial potential at the conductor-electrolyte interface and the portion of the faradaic current flowing through the interface. As will be apparent to those skilled in art of bipolar electrolysis, current flow through the conductor is dependent on the following factors: (1) the conductivity of the electrolyte solution, (2) the electrically conductive material used for the conductor, (3) the longest dimension of the conductor oriented along the current flow lines, (4) the free space of the current path in the electrolyte solution around the conductor, (5) the character of the electrode process occurring at the interface, and (6) the interfacial resistance between the conductor and the solution. Thus, varying parameters such as the size, shape, orientation, location or material of the conductor will affect the requisite voltage to be applied to the current-delivering electrodes to induce luminescence. These parameters can easily ascertained by one skilled in the art following the teachings of the present invention.

The resulting light intensity is measured on the wavelength and/or time-resolved basis for a period necessary to achieve the required signal-to-noise ratio, and used for the quantification of the luminescent compound. The light detector is any light-detecting device, such as a photomultiplier or a photodiode with an optical filter or monochromator. Optionally, the light-detecting device can be connected with an amplifier where the electrical signal from the light detector is amplified. The concentration of the ECL moiety is determined by standard analysis techniques known in the art.

In a preferred embodiment, the method of the present invention is used to measure an analyte of interest. As with other known ECL assays, the ECL moiety is used as a labeling agent to quantify the concentration of an analyte of interest. The ECL moiety may be bound as a labeling agent to the analyte of interest or to a reagent used to ascertain the presence of the analyte (e.g., an antigen or antibody in immunoassays). Accordingly, the method of the present invention is particulary suitable for use with analytical methods having low detection limit requirements. Examples of such analytical methods include, but are not limited to, binding assays such as immunoassays, nucleic acid hybridization assays, releasing assays, back titration assays and detection systems used in chromatography, capillary electrophoresis and flow injection analysis.

For example, the method of the present invention is used as an immunoassay to determine the concentration of an antigen or multiple antigens. The antigen is quantified by incubating a conductor or multiple conductors having immobilized thereon a primary antibody with the antigen-containing sample and subsequently with a secondary antibody bound to an ECL moiety. After incubation for a sufficient amount of time, the conductor or conductors are washed in which unbound labeled antibodies are washed away. The conductor or conductors are subsequently placed in a cell between current-delivering electrodes, in which luminescence is induced and measured in accordance with the present invention.

Various modifications of the above-described immunoassay can be used. For example, using time-resolved or spectral discrimination two or more labeled compounds can be simultaneously detected. The above-described double labeling can be extended to noncompetitive assays where the secondary antibody is labeled with different ECL moieties to achieve the internal standardization of the assay. Alternatively, two or more different labeling compounds can be used thus requiring different electrolytes for the generation of luminenscence. By changing the electrolyte, different labeling compounds and analytes on the same or different conductors can be quantified one after another.

Likewise, variations in the size or material of the conductors allows for the simultaneous measurement of different luminescent compounds and determining the concentration of different analytes in a sample. For example, two conductors of different sizes may be coated with different primary antibodies. The conductors are then incubated with a mixture containing two different antigens to be quantified and two secondary antibodies labeled with the same ECL moiety. After a sufficient amount of time, the conductors are washed to remove the unbound secondary antibodies. The conductors are then placed in a cell where luminescence is induced by gradually increasing the voltage applied to the current-delivering electrodes. As the voltage is gradually increased, light is emitted at the larger conductor first since it has a lower threshold potential than its smaller counterpart. Once the voltage drop in the electrolyte solution is high enough, light then begins to emit at the smaller conductor. Other modifications of the method of the present invention can be easily ascertained by those skilled in the art.

EXAMPLES

Figure 1:
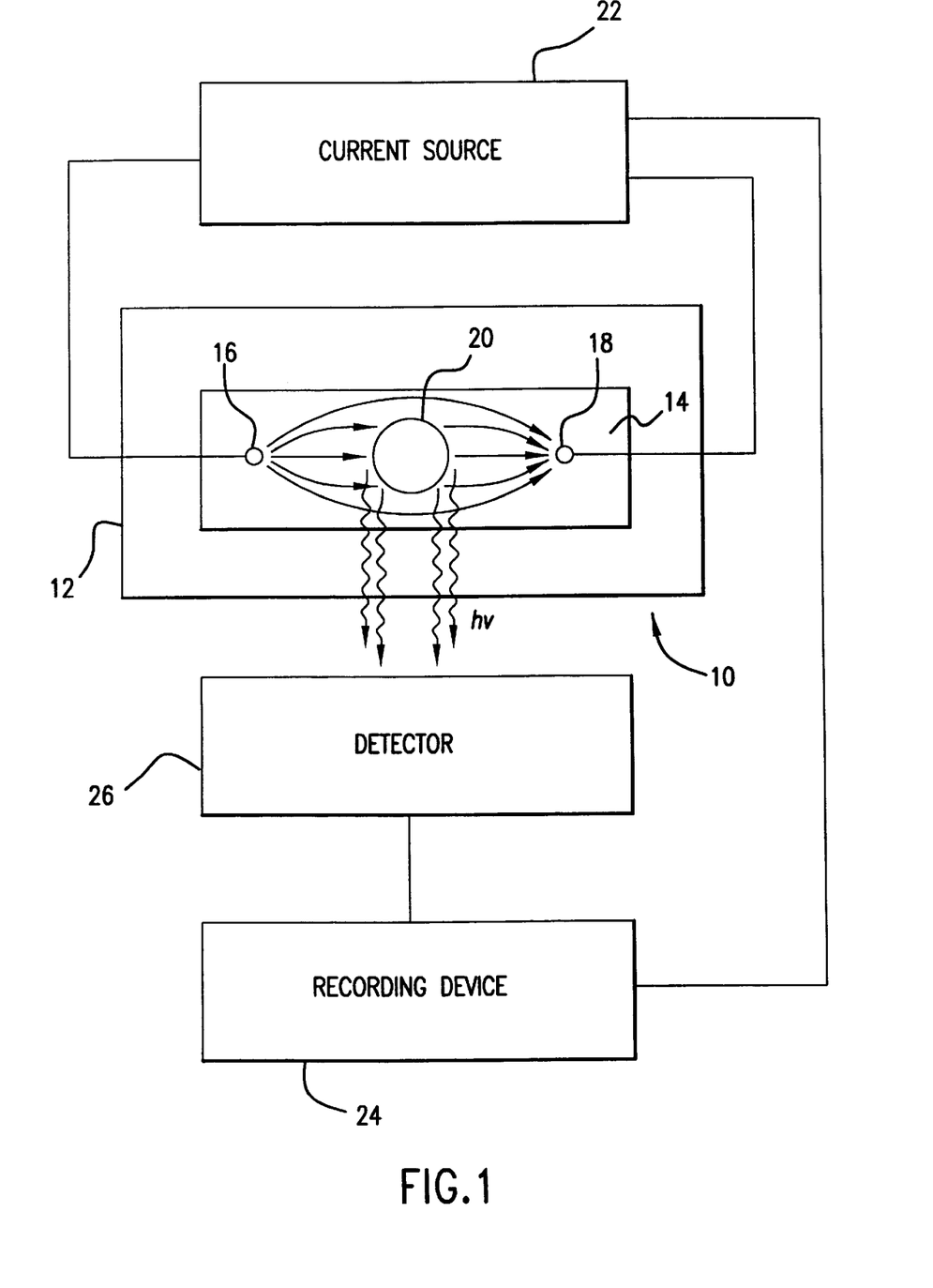
FIG. 1 is a block diagram of the contactless electrogenerated luminescence apparatus with a single electrically conductive material.

The following non-limiting examples illustrate the use of contactless electrogenerated luminescence (COEL). FIG. 1 shows a generalized diagram of the apparatus to be used in accordance with the invention. Referring to FIG. 1, a cell (10) is provided having cells walls (12) enclosing an electrolyte (14). The electrolyte (14) has immersed therein a pair of current-delivering electrodes (16, 18) and a conductor (20) position between the electrodes, but not in electronic contact with the electrodes. Connected to the electrodes (16, 18) is a current source (22) that is also connected to a recording device (24), which in turn is connected to a light detector (26) to detect the light (hv) emitted at the conductor.

The cell used in the following examples was a polytetrafluoroethylene cell having the dimensions: L=16 mm, W=7 mm, D=9 mm. The current-delivering electrodes were made of stainless steel wire having a diameter of 2 mm. The electrodes were spaced 11 mm apart from each other. The current source was a home-made coulostatic pulse generator capable of generating square pulses of 60 volts (V) and 0.4 milliseconds (ms). The light detector was a Hamamatsu photomultiplier, Model No. R3550. The detected signal was amplified with a Stanford Research preamplifier, Model No. SR455. The amplified signal was counted with a Stanford Research photon counter, Model No. SR400. The photon counter was connected coupled to a PC-computer for controlling the measuring system and data storage.

Although electric current is the primary factor for the voltage drop at the conductors and thus for the generation of luminescence, due to the instrumental reasons only the voltage applied to the current-delivering electrodes is mentioned in the Examples 1 to 6.

Example 1

Contactless Electrogenerated Luminescence with Luminol

Figure 2:
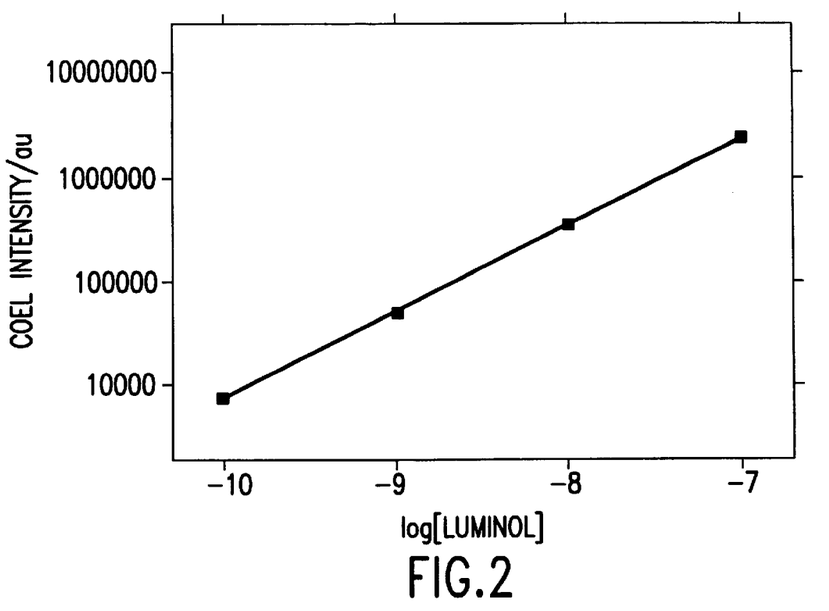
FIG. 2 is a plot graph of luminenscence as a function of luminol concentration measured by contactless electrogenerated luminescence.

Sample solutions were prepared from the following components: $5.0 \times 10^{-2}$ borate buffer adjusted to pH 7.8, $7.1 \times 10^{-2}$ M sodium azide and varying amounts of luminol (i.e., 5-amino-2,3-dihydro-1,4-phthalazinedione). The contactless electrogenerated luminescence (COEL) was initiated at the surface of a spherical 6.3-mm diameter aluminum conductor (Al-conductor) (AbbotBall Company) as follows: excitation pulses of 0.4 ms duration and 60 V amplitude with the intermittent 10 ms zero level were applied to the current-delivering electrodes resulting in an approximately 50 mA peak current in the sample solution. The resulting light emission (i.e., COEL response) from the Al-conductor was detected by the photomultiplier. The integrated COEL response from the 500 excitation pulses as a function of luminol concentration in the sample solutions are presented in Table 1 and FIG. 2. The background COEL response (i.e., the response without the Al-conductor in the sample cell) was around 50 times lower than the analogous background COEL response in Table 1.

TABLE 1

COEL response as a function of luminol concentration

| [Luminol]/mol $1^{-1}$ | COEL/au |
|---|---|
| 0 | 7563 |
| $1.0 \times 10^{-11}$ | 7490 |
| $1.0 \times 10^{-10}$ | 15839 |
| $1.0 \times 10^{-9}$ | 58352 |
| $1.0 \times 10^{-8}$ | 363900 |
| $1.0 \times 10^{-7}$ | 2381000 |

Example 2

Contactless Electrogenerated Luminescence with $Ru(bpy)_3^{2+}$

Figure 3:
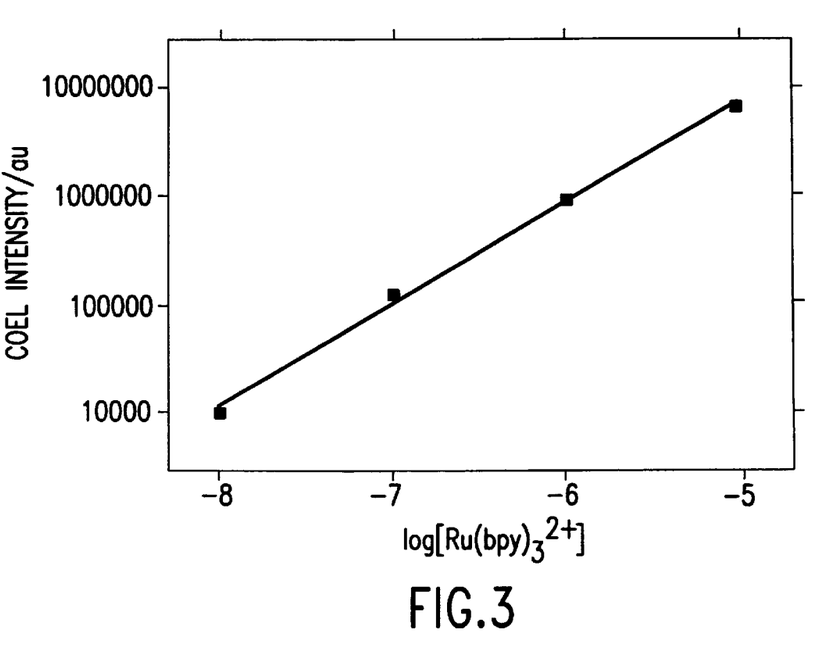
FIG. 3 is a plot graph of luminenscence as a function of $Ru(bpy)_3^{2+}$ concentration measured by contactless electrogenerated luminescence.

Sample solutions were prepared from the following components: $1.12 \times 10^{-1}$ M potassium dihydrogen phosphate and $8.80 \times 10^{-2}$ M dipotassium hydrogen phosphate buffer at pH 7.2, $1.0 \times 10^{-1}$ M tripropylamine, $7.1 \times 10^{-2}$ M sodium azide and varying amounts of tris(2,2'-bipyridyl)ruthenium(II) $(Ru(bpy)_3^{2+}$. The contactless electrogenerated luminescence (COEL) was initiated at the surface of a spherical 5.0-mm diameter gold conductor (Au-conductor) (i.e., a glass ball covered with a vacuum evaporated gold layer) as follows: excitation pulses of 0.4 ms duration and 6.0 V amplitude with the intermittent 10 ms zero level were applied to the current-delivering electrodes resulting in an approximately 50 mA peak current in the said sample solution. The resulting light emission (i.e., the COEL response) from the Au-conductor was detected by the photomultiplier. The integrated COEL response from the 500 excitation pulses as a function of $Ru(bpy)_3^{2+}$ concentration in the samples solution are presented in Table 2 and FIG. 3. The background COEL response (i.e., the response without the Au-conductor in the sample cell) was around 50 times lower than the analogous background COEL response in Table 2.

TABLE 2

COEL response as a function of $Ru(bpy)_3^{2+}$ concentration

| $[Ru(bpy)_3^{2+}]$/mol $1^{-1}$ | COEL/au |
|---|---|
| 0 | 853 |
| $1.0 \times 10^{-8}$ | 11025 |
| $1.0 \times 10^{-7}$ | 131540 |
| $1.0 \times 10^{-6}$ | 942059 |
| $1.0 \times 10^{-5}$ | 6715220 |

Example 3

Contactless Electrogenerated Luminescence with Terbium(III)-1

Figure 4:
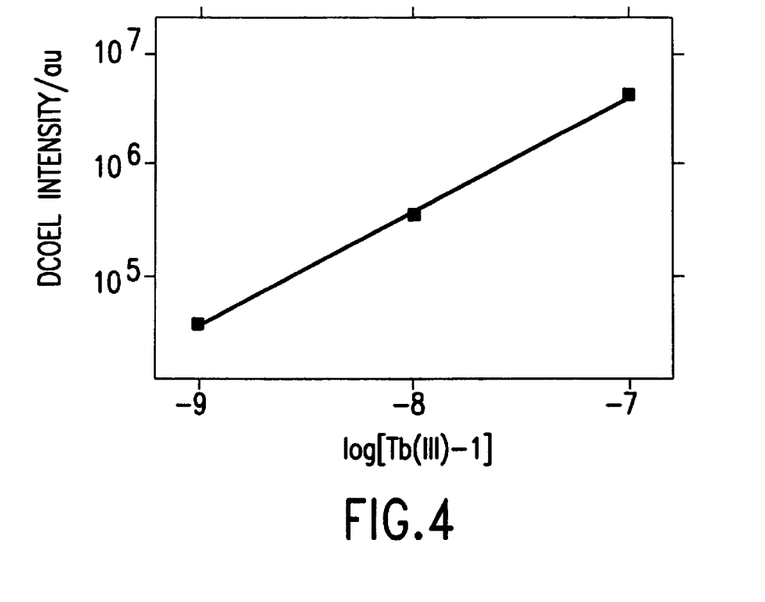
FIG. 4 is a plot graph of luminenscence as a function of terbium(III) concentration measured by delayed contactless electrogenerated luminescence.

Sample solutions were prepared from the following components: $5.0 \times 10^{-2}$ M borate buffer adjusted to pH 7.8, $7.1 \times 10^{-1}$ M sodium azide and varying amounts of Tb(III)-1 chelate where 1 is 2,6-bis[N,N-bis(carboxymethyl)

aminomethyl]-4-benzoylphenol. COEL was initiated at the surface of a spherical 6.3-mm diameter Al-conductor (AbbotBall Company) as follows: excitation pulses of 0.4 ms; duration and 60 V amplitude with the intermittent 100 ms zero level were applied to the current-delivering electrodes resulting in an approximately 50 mA current in the said sample solutions. The resulting light emission from the Al-conductor was detected by the photomultiplier during the 0.08–8.0 ms interval from the end of the 0.4-ms excitation pulse (i.e., a delayed COEL or, abbreviated, a DCOEL response). The integrated DCOEL response from the 500 excitation pulses as a function of terbium(III) concentration in the sample solutions are presented in Table 3 and FIG. 4. The background DCOEL response (i.e., the response without the Al-conductor in the sample cell) was around 5000 times lower than the analogous background DCOEL response in Table 3.

TABLE 3

DCOEL response as a function of terbium(III)-1 concentration

| [Tb(III)-1]/mol $l^{-1}$ | DCOEL/au |
| --- | --- |
| 0 | 10054 |
| $1.0 \times 10^{-9}$ | 46499 |
| $1.0 \times 10^{-8}$ | 337576 |
| $1.0 \times 10^{-7}$ | 4001260 |

Example 4

Immunoassay of Human Thyroid Stimulating Hormone (hTSH) by the Contactless Electrogenerated Luminescence A. Preparation of Labeling Compound A terbium(III) complex with 4-(3-isothiocyanatobenzoyl)-2,6-bis[N,N-bis(carboxymethyl) aminomethyl]phenol was used as the labeling compound and was synthesized as set forth in J. Kankare et al., *Anal. Chin. Acta*, 266:205 (1992), which is incorporated herein by reference.

B. Labelling of anti-hTSH IgG

A 60-fold excess of 4-(3-isothiocyanatobenzoyl)-2,6-bis [NN-bis(carboxymethyl)aminomethyl]phenol terbium(III) complex was allowed to react overnight with anti-hTSH IgG (Oy Medix Biochemica Ab, Kauniainen, Finland) at pH 9.5. The labeled antibody was separated from the excess free terbium(III) complex on a column filled with Sephadex G-50 (1.0×5.5 cm) and Sepharose 6 B (1.0×5.2 cm) by using $1.0 \times 10^{-1}$ M sodium carbonate buffer at pH 9.3, containing 9 g $l^{-1}$ of sodium chloride and 0.05% sodium azide as the eluting agent.

C. Coating of the Aluminum-conductors

The 6.3-mm diameter Al-conductors (AbbotBall Company) were coated with anti-hTSH IgG by a physical adsorption with $5.0 \times 10^{-2}$ M Tris-HCl buffer at pH 7.5, containing 9 g $l^{-1}$ sodium chloride and 0.05% sodium azide. The reaction mixture was left overnight at ambient temperature. After coating, the Al-conductors were washed with a solution containing 9 g $l^{-1}$ sodium chloride, 0.01% sodium azide 0.2 g $l^{-1}$ Tween, and saturated with 0.1% BSA (bovine serum albumin) for overnight and stored wet at 4° C.

D. Immunoassay of hTSH

Figure 5:
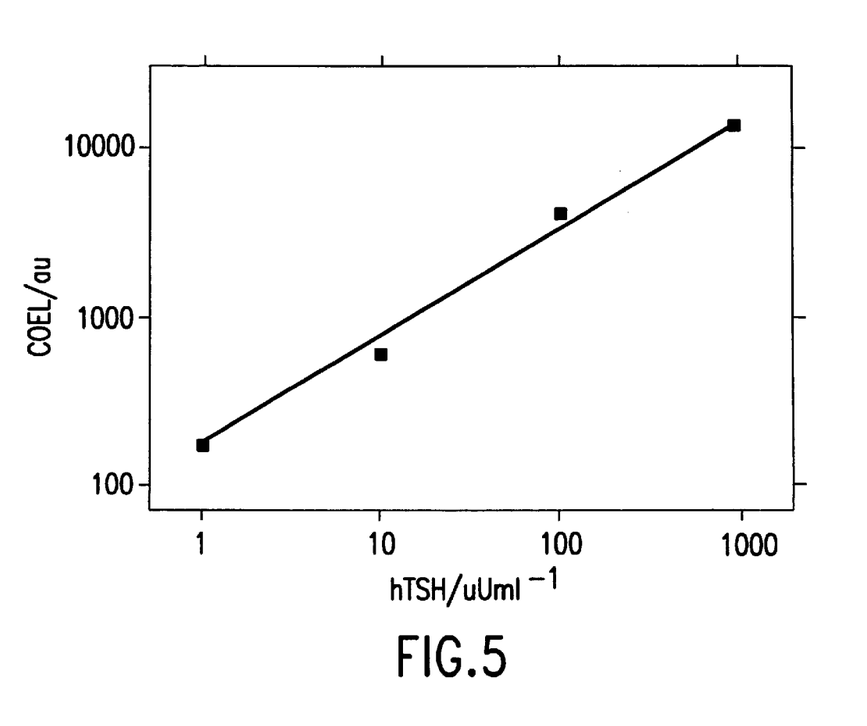
FIG. 5 is a plot graph of luminenscence as a function of human Thyroid-Stimulating-Hormone (hTSH) concentration measured by the delayed contactless electrogenerated luminescence.

A 100-μl aliquot of an appropriate standard containing 0, 1, 10, 100 or 1000 μU $ml^{-1}$ of hTSH (Orion Diagnostica, Espoo, Finland) was added into a 300-μl test tube followed by 14.5 μl of terbium(III)-labeled anti-hTSH solution where 23.4 μg $ml^{-1}$ of the terbium(III)-labeled anti-hTSH was dissolved in 5.064 ml of $5.0 \times 10^{-2}$ M TRIS-$H_2SO_4$ buffer at pH 7.8 containing additionally 9 g $l^{-1}$ sodium chloride, 5 g $l^{-1}$ BSA, 0.5 g $l^{-1}$ sodium azide, 0.5 g $l^{-1}$ bovine γ-globulin, 0.1g $l^{-1}$ Tween 20, 7.9 mg $l^{-1}$ DTPA (diethylenetriaminpentaacetic acid). The coated and washed Al-conductor was placed in the aforementioned test tube. After one-hour incubation by continuously shaking, the Al-conductor was washed twice for 2 minutes with 400 μl $5.0 \times 10^{-2}$ M TRIS-HCl buffer at pH 7.4 containing additionally 0.05% sodium azide, 0.2% BSA, 0.1% Tween. The Al-conductor was then transferred to the COEL cell containing $5.0 \times 10^{-2}$ M $H_3BO_3$—$H_2SO_4$ buffer at pH 7.8 and $1.0 \times 10^{-2}$ M sodium azide. The DCOEL response was measured following the procedure of Example 3 and the results are presented in Table 4 and FIG. 5.

TABLE 4

Immunoassay of hTSH by the contactless electrogenerated luminescence

| hTSH/μU $ml^{-1}$ | DCOEL/au |
| --- | --- |
| 0 | 471 |
| 1 | 650 |
| 10 | 1070 |
| 100 | 4380 |
| 1000 | 13620 |

Example 5

Multicomponent Analysis by Contactless Electrogenerated Luminescence

Figure 6:
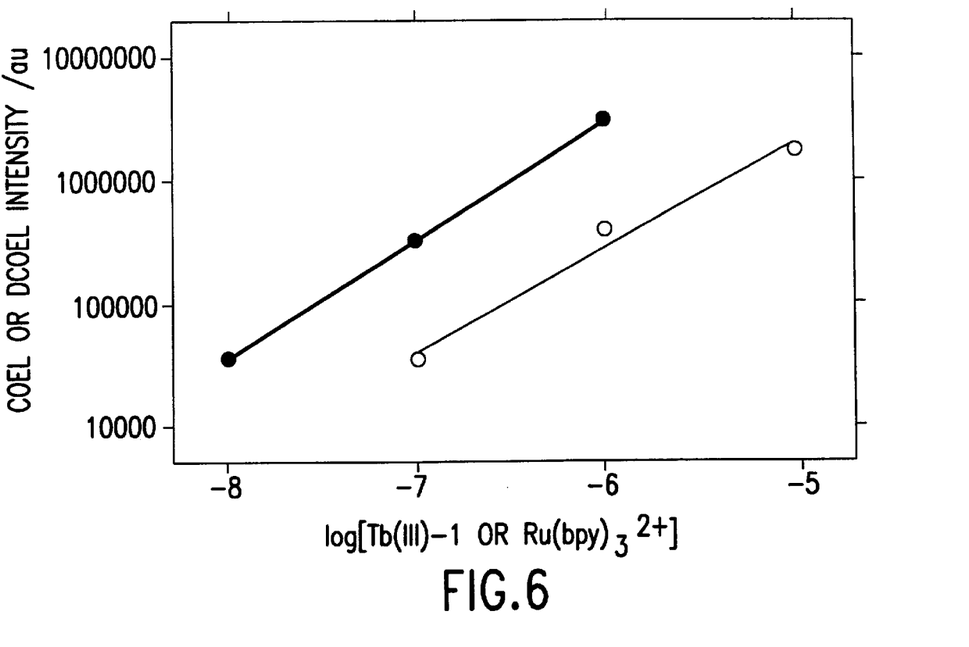
FIG. 6 is a plot graph of Tb(III) (●) and $Ru(bpy)_3^{2+}$ (○) concentrations in a sample mixture measured by contactless and delayed contactless electrogenerated luminescence, respectively.
Figure 7:
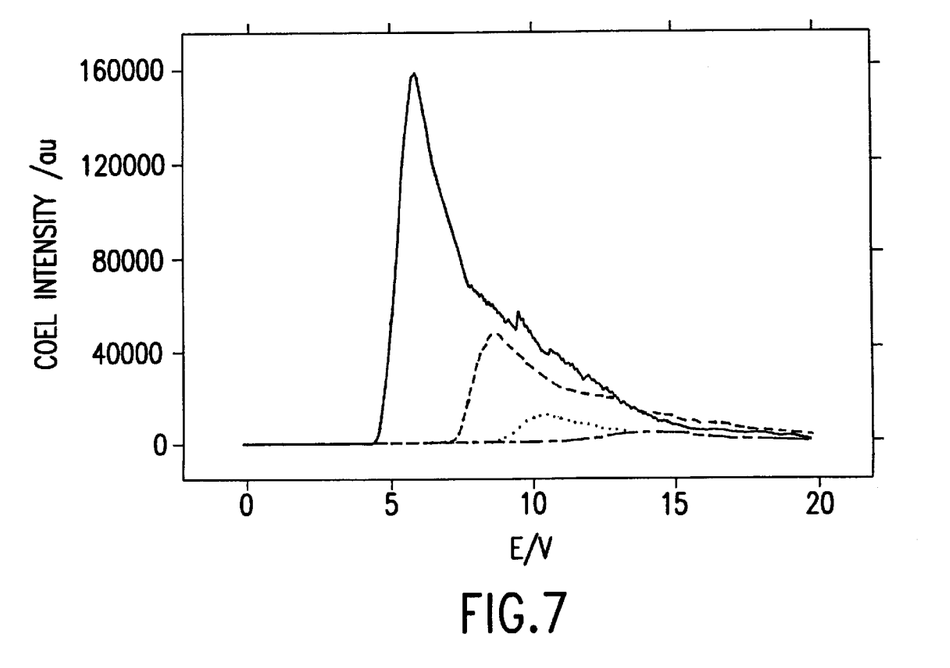
FIG. 7 is a composite electroluminogram of $Ru(bpy)_3^{2+}$ illustrating the effect on luminescence by varying the diameter of spherical Au-conductors: 2.0 mm (-··-); 2.5 mm (······); 3.5 mm (---); and 6.0 mm (—).

Sample solutions were prepared from the following components: $5.0 \times 10^{-2}$ M borate buffer adjusted to pH 7.8, $3.0 \times 10^{-3}$ M peroxydisulfate and $1.0 \times 10^{-3}$ M Tween (polyoxyethylene(20) sorbitan monolaurate) and varying amounts of $Ru(bpy)_3^{2+}$ and Tb(III)-1 chelate. COEL was initiated at the surface of a spherical 6.3-mm diameter Al-conductor (AbbotBall Company) as follows: excitation pulses of 0.4 ms duration and 60 V amplitude with the intermittent 100 ms zero level were applied to the current-delivering electrodes resulting in an approximately 50 mA current in the said sample solution. The resulting light emission from the Al-conductor was detected by the photomultiplier during the excitation pulse (i.e., a COEL response) and during the 0.08–8.0 ms interval from the end of the 0.4-ms excitation pulse (i.e., a delayed COEL or DCOEL response). The integrated COEL and DCOEL responses from the 500 excitation pulses are presented in Table 5 and FIG. 6: the DCOEL response can be used for the quantification of Tb(III)-1 in these sample mixtures because the COEL of $Ru(bpy)_3^{2+}$ was too short-lived to reach the 0.08–8.0 ms detection window, while the listed COEL response (i.e., the observed COEL response subtracted by the COEL response of Tb(III)-1 which, in turn, is estimated from its measured DCOEL response) can be used for the quantification of $Ru(bpy)_3^{2+}$.

TABLE 5

COEL and DCOEL response as a function
of combined Tb(III)-1 and Ru(bpy)$_3^{2+}$ concentrations

| [Tb(III)-1 + [Ru(bpy)$_3^{2+}$]/mol$^{-1}$ | COEL of Ru(bpy)$_3^{2+}$/au | DCOEL of Tb(III)-1/au |
|---|---|---|
| $1.0 \times 10^{-8} + 1.0 \times 10^{-6}$ | 335772 | 36377 |
| $1.0 \times 10^{-7} + 1.0 \times 10^{-6}$ | 382782 | 317303 |
| $1.0 \times 10^{-6} + 1.0 \times 10^{-6}$ | 1383670 | 2933600 |
| $1.0 \times 10^{-7} + 1.0 \times 10^{-7}$ | 34376 | 377757 |
| $1.0 \times 10^{-7} + 1.0 \times 10^{-6}$ | 382782 | 317303 |
| $1.0 \times 10^{-7} + 1.0 \times 10^{-5}$ | 1697352 | 395255 |

Example 6

Size-selective Contactless Electrogenerated Luminescence

A sample solution was prepared from the following components: $1.12 \times 10^{-1}$ M potassium dihydrogen phosphate and $8.80 \times 10^{-2}$ M dipotassium hydrogen phosphate buffer at pH 7.2, $1.0 \times 10^{-1}$ M tripropylamine, $7.1 \times 10^{-2}$ M sodium azide and $1.0 \times 10^{-8}$ M tris(2,2'-bipyridyl)ruthenium(II) (Ru(bpy)$_3^{2+}$). COEL was separately initiated at the surface of spherical gold conductors (Au-conductors) with the diameters listed in Table 6 (i.e., a glass ball covered with a vacuum evaporated gold layer) by applying a DC excitation voltage from 0 V to 20 V to the current-delivering electrodes at a sweep rate of 0.25 V s$^{-1}$ in the sample solution. The resulting COEL responses of Ru(bpy)$_3^{2+}$ from the different Au-conductors was detected by the photomultiplier and are displayed in FIG. 6 (2.0 mm (-·-), 2.5 mm (······), 3.5 mm (---) and 6.0 mm (—)). The peak voltages and intensities of the COEL of Ru(bpy)$_3^{2+}$ using the different Au-conductors are listed in Table 6.

TABLE 6

Peak voltages and peak intensities of the Ru(bpy)$_3^{2+}$ COEL
in the electroluminograms obtained using different Au-conductors

| Diameter of Au-conductor/mm | Peak Voltage/V | COEL of Ru(bpy)$_3^{2+}$/au |
|---|---|---|
| 2.0 | 14.0 | 4600 |
| 2.5 | 10.5 | 10600 |
| 3.5 | 8.9 | 46300 |
| 6.0 | 5.7 | 157000 |

We claim:

1. A method of generating luminescence of a luminescent compound for quantification of said luminescent compound, which comprises:
   providing an electrolyte having therein (i) a pair of current-delivering electrodes, (ii) an electrically conductive material positioned between said electrodes, but not in electronic contact with said electrodes, and (iii) said luminescent compound being in electronic contact with said electrically conductive material; and
   applying an electric current to said electrodes thereby inducing said luminescent compound to luminesce.

2. The method according to claim 1, wherein said method further comprises measuring said luminescence to quantify the concentration of said luminescent compound.

3. The method according to claim 1, wherein said electrically conductive material is electrochemically inert material.

4. The method according to claim 3, wherein said electrochemically inert material is glassy carbon, gold, platinum, or mixtures thereof.

5. The method according to claim 1, wherein said electrically conductive material is an insulated metal or semi-metal.

6. The method according to claim 5, wherein said insulated metal or semi-metal is insulated with an oxide or polymeric coating.

7. The method according to claim 5, wherein said metal or semi-metal is aluminum, hafnium, magnesium, silicon, tantalum, titanium, zirconium, or mixtures thereof.

8. The method according to claim 1, wherein said electrically conductive material is a porous membrane covered with a thin layer of an electrochemically inert material or an insulated metal or semi-metal.

9. The method according to claim 1, wherein said electrically conductive material is a combination of an electrochemically inert material and an insulated metal or semi-metal.

10. The method according to claim 1, wherein said electrolyte contains at least two electrically conductive materials.

11. The method according to claim 1, wherein said electrolyte contains at least two different types of electrically conductive materials.

12. The method according to claim 1, wherein the said electrolyte is an aqueous electrolyte.

13. The method according to claim 1, wherein the said electrolyte is a non-aqueous electrolyte.

14. The method according to claim 1, wherein said luminescent compound is attached to the surface of the said electrically conductive material.

15. The method according to claim 1, wherein said luminescent compound is bound to analyte of interest.

16. The method according to claim 1, wherein said luminescence is measured after a delay from the end of said electric current being applied to the said current-delivering electrodes.

17. The method according to claim 15, wherein said luminescence results from at least two different luminescent compounds.

18. A method according to claim 15, wherein the said luminescence is formed at the surface of at least two different types of electrically conductive materials.

19. A method according to claim 18, wherein said luminescence on the surfaces of said different electrically conductive materials is initiated and measured at different current levels passing through the current-delivering electrodes.

20. The method according to claim 17, wherein measurements of two or more chemiluminescent compounds on different conductors are used for internal standardization.

21. The method according to claim 18, wherein measurements of two or more luminescent compounds on different conductors are used for determining the concentration of two or more analytes.

22. The method according to claim 15, wherein said analyte of interest is a nucleic acid sequence.

23. The method according to claim 15, wherein said analyte is an amino acid sequence.

* * * * *